United States Patent [19]
Wong et al.

[11] Patent Number: 5,947,911
[45] Date of Patent: *Sep. 7, 1999

[54] METHOD AND APPARATUS FOR REDUCING PURGE VOLUME IN A BLOOD CHEMISTRY MONITORING SYSTEM

[75] Inventors: David K. Wong, Del Mar; Benjamin B. Lai, San Diego, both of Calif.

[73] Assignee: Via Medical Corporation, San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/780,799

[22] Filed: Jan. 9, 1997

[51] Int. Cl.⁶ .................................................. A61B 5/00
[52] U.S. Cl. ..................... 600/573; 600/309; 600/322; 604/4; 604/131
[58] Field of Search .................................. 600/309, 322, 600/345, 573; 604/4, 49, 50, 51, 52, 53, 131; 204/403, 409, 411

[56] References Cited

U.S. PATENT DOCUMENTS

| | | | |
|---|---|---|---|
| 4,293,307 | 10/1981 | Simpson et al. | 23/230 B |
| 4,573,968 | 3/1986 | Parker | 604/52 |
| 5,048,537 | 9/1991 | Messinger | 604/52 |
| 5,123,901 | 6/1992 | Carew | 604/5 |
| 5,165,406 | 11/1992 | Wong | 600/573 |
| 5,271,815 | 12/1993 | Wong | 204/153.12 |
| 5,324,266 | 6/1994 | Ambrisco et al. | 604/125 |
| 5,330,634 | 7/1994 | Wong et al. | 204/409 |
| 5,403,285 | 4/1995 | Roberts | 604/179 |
| 5,505,828 | 4/1996 | Wong et al. | 205/777.5 |
| 5,531,672 | 7/1996 | Lynn | 604/4 |
| 5,554,114 | 9/1996 | Wallace et al. | 604/53 |
| 5,665,312 | 9/1997 | Sperber et al. | 422/81 |

FOREIGN PATENT DOCUMENTS 0 004 760 A2  10/1979  European Pat. Off. ....... G01N 33/16

*Primary Examiner*—Max Hindenburg
*Assistant Examiner*—Charles Marmor, II
*Attorney, Agent, or Firm*—Sheppard, Mullin, Richter & Hampton; James R. Brueggemann

[57] ABSTRACT

A method and apparatus for reducing the volume of fluid required to purge a patient's blood from a blood sampling site after the blood has been sampled for measurement. A coil is formed in the fluid flow line between the source of fluid and the blood sampling site by looping the fluid flow line around on itself in order to generate turbulence in the fluid flow to help purge the patient's blood from the blood sampling site after sampling. This turbulence-inducing coil is conveniently formed in a fluid flow line extending from the upstream end of a blood chemistry sensor module which is adapted to be installed in the fluid flow line of a standard IV infusion set as part of a combined infusion fluid delivery and blood chemistry monitoring system.

11 Claims, 1 Drawing Sheet

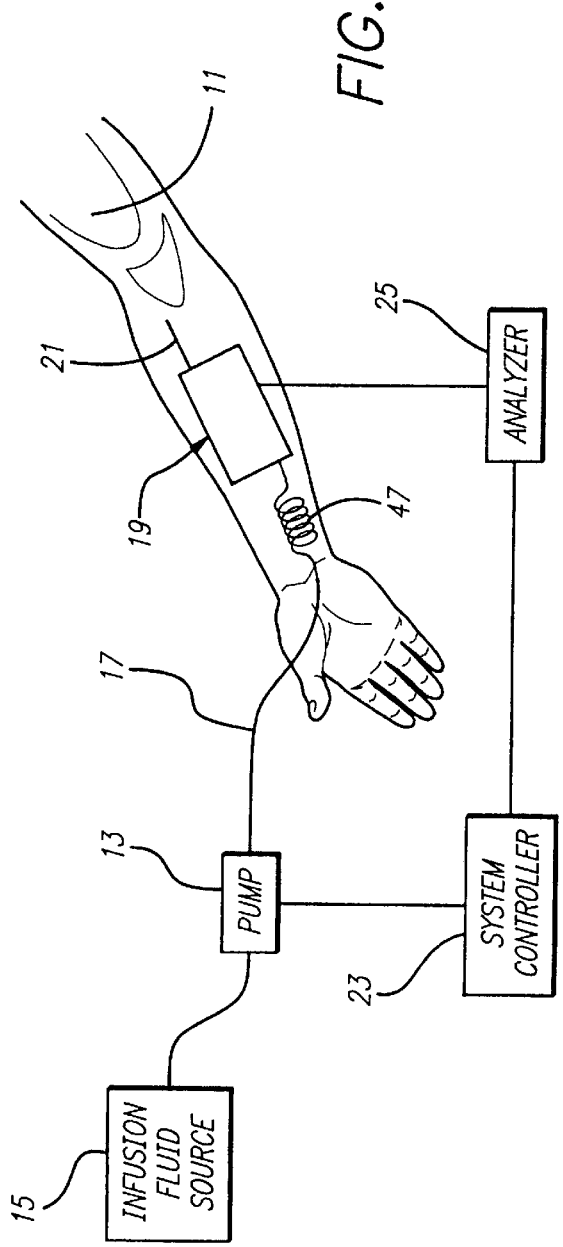
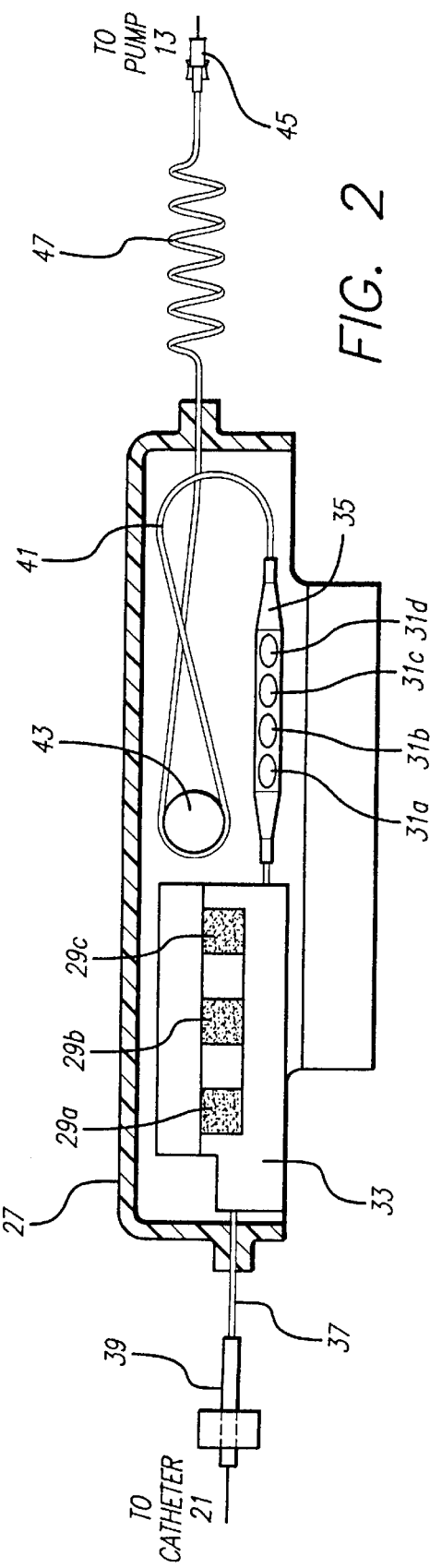

METHOD AND APPARATUS FOR REDUCING PURGE VOLUME IN A BLOOD CHEMISTRY MONITORING SYSTEM

BACKGROUND OF THE INVENTION

This invention relates generally to blood chemistry monitoring systems and, more particularly, to a method and apparatus for reducing the volume of fluid required to purge a patient's blood from a blood sampling site after the blood has been sampled for measurement.

The invention is particularly suitable for use with a system that infuses a fluid into a patient substantially continuously, wherein some provision is made in the system for blood chemistry measurement. Such infusion delivery systems are connected to a patient at an intravenous (IV) port, in which a hollow needle/catheter combination is inserted into a blood vessel of the patient and an infusion fluid is introduced into the vessel at a controlled rate from an IV bottle or other source of fluid via a fluid flow line or infusion tube. The rate of infusion may be controlled by a simple manual clamp or by an electromechanical infusion pump or controller acting on the fluid flow line.

It is common practice to remove blood from a blood vessel for analysis while the patient is undergoing IV infusion. Typically, a mixture of blood and infusion fluid is removed from a blood sampling port in the fluid flow line with a first syringe to allow undiluted blood to reach the stopcock (?). A second syringe is used to take a blood sample to the laboratory for analysis. The fluid flow line is then purged with the infusion fluid to flush the blood in the fluid flow line back into the patient. The amount of infusion fluid required to flush the fluid flow line clean is a function of purge rate and the amount of blood in the fluid flow line. In a typical infusion delivery system of this type, it is not unusual to flush the line at a rate greater than 1,000 ml/hour with more than 6 to 10 times of the volume of he blood to be flushed back into the patient.

In recent years, automatic blood chemistry monitoring systems have been developed which may be combined with infusion delivery systems of this kind, using the IV port to periodically withdraw a blood sample, perform measurements of various characteristics of the blood, and then reinfuse the blood into the patient. The system then resumes normal delivery of the infusion fluid. Such a system is described in U.S. Pat. No. 4,573,968. In that system, an infusion pump normally pumps a suitable infusion fluid via an infusion tube and catheter into a patient, but intermittently reverses its direction, to draw a sample of blood from the patient through the catheter and into a sensor assembly connected to the infusion tube. The physical configuration of one suitable sensor assembly is disclosed in U.S. Pat. No. 5,165,406. The sensor assembly includes a plurality of sensors that produce electrical signals corresponding to various conditions or parameters of the patient's blood. Examples of such parameters include concentrations of carbon dioxide, oxygen, potassium, calcium, and sodium, as well as hematocrit and pH. These signals are supplied to a analyzer, which converts the signals into a form readable by a caregiver.

With blood chemistry monitoring systems as described above, adequate purging of blood from the sensor assembly is a special concern. The accuracy of the blood chemistry measurement can be adversely affected by blood cells and other blood components (e.g., protein) that build up in the various spaces and crevices of the sensor assembly. That is, the accumulation of extraneous blood cells around the sensor electrodes can result in erroneous calibration and inaccurate measurement of blood chemistry. To avoid this problem, successive measurements generally cannot be taken unless the sensor assembly has been thoroughly purged of blood cells between measurements. Thus, a specified purge volume of infusion fluid must be passed through the sensor assembly after each measurement.

For example, such a blood chemistry monitoring system will draw 0.5 to 1.5 ml of blood as a sample. This is considerably more than the minimum amount required to reach the sensors in the sensor assembly, but it ensures that the sensors are exposed to essentially undiluted blood. A method and apparatus for precisely and repeatably drawing a sufficient blood sample to ensure that it reaches all of the sensor assembly's individual sensors and that sufficient additional blood is drawn to minimize the dilution effects of an adjacent infusion fluid is disclosed in co-pending application Ser. No. 08/688,153, filed Jul. 29, 1996, and assigned to the same assignee as the present application. However, such a blood sample then requires about 5 to 10 ml of infusion fluid (i.e., 6 to 10 times the blood drawn for the sample) at rate of 900 ml/hour to purge the sensor assembly. This volume is well within the fluid intake range of most patients, but for volume-restricted adults and pediatric and neonatal patients, this volume is excessive. Furthermore, if a patient requires more frequent monitoring (e.g., every 15 minutes), purging would require up to 1,200 ml of infusion fluid per day.

In an effort to reduce the blood fouling problem described above and the amount of infusion fluid required for purging, it is known to provide a smooth flow path in the sensor assembly. Some assemblies, for example, provide flush-mounted sensor electrodes, in which the electrodes are located in a sensor cavity and a water soluble reference material or gel is placed above the electrode and a polymer-based, selectively-permeable material is placed on top of the gel to form a smooth flow pathway for samples. The selectively-permeable material presents a smooth outer surface to the fluid flow, flush with the electrode housing, and it allows only selected ions to reach the reference gel and thereby produce a reading from the electrode. Such flush-mounted electrode designs, however, can be difficult to manufacture. To provide accurate readings, a precise separation must be provided between the aqueous-based internal reference gel and the polymerbased selectively permeable material, and the electrode must be kept free of any contact with the fluid being measured. Such separation is difficult to maintain due to wicking of the reference gel, which causes it to spread to areas of the sensor cavity where the selectively-permeable layer will be deposited. This can allow the fluid being measured to reach the electrode, shorting the electrode out.

Another proposed solution to the problem is described in the aforementioned U.S. Pat. No. 5,165,406, in which the sensor assembly has an internal conduit with a turbulence structure in the form of a helical groove disposed upstream of the sensor electrodes and in the fluid flow path. This is intended to create turbulence in the flow of fluid through the sensor assembly, which in turn is intended to promote dislodging of any blood cells collected around the sensor electrodes, without appreciably increasing turbulence between the blood and infusion fluid upstream of the sensor assembly when the sample is being taken. However, due to its cost of manufacture and other concerns, this proposed solution has never been implemented in any commercial blood chemistry monitoring system.

From the foregoing discussion, it should be apparent that there is need for more efficient, effective and clinically safe purging of blood samples in infusion fluid delivery systems that avoids collection of blood cells and reduces purge volumes, thereby also reducing the time intervals between successive measurements. The present invention satisfies this need.

SUMMARY OF THE INVENTION

Briefly, and in general terms, the present invention resides a method and apparatus for reducing the volume of fluid required to purge a patient's blood from a blood sampling site after the blood has been sampled for measurement. The invention may have application to a variety of devices for sampling bodily fluids where conservation of fluid flushing volumes is a concern, but it has particular use as part of a combined infusion delivery and blood chemistry monitoring system that substantially continuously infuses an infusion fluid into patient, while intermittently reversing itself and drawing blood samples from the patient into a blood chemistry sensor assembly, for analysis.

More specifically, the present invention includes a coil formed in the fluid flow line between the source of fluid and the blood sampling site by looping the fluid flow line around on itself. The coil generates turbulence in the fluid flow to help purge the patient's blood from the blood sampling site after sampling. The coil may comprise one or more loops of the fluid flow line permanently formed in a spiral and having a diameter of less than about two inches. However, any number of other arrangements of the loops are possible so long as the requisite turbulence is imparted to the fluid flow through the fluid flow line. In a presently preferred embodiment, the coil comprises at least three loops of the fluid flow line in a spiral having a diameter between 0.75 and 1.0 inch.

For use in a combined infusion fluid delivery and blood chemistry monitoring system of the type described above, the invention may be embodied most conveniently in a blood chemistry sensor module which is adapted to be installed in the fluid flow line of a standard IV infusion set. The module includes a sensor housing having an upstream end and a downstream end. A first fluid flow line extends from the downstream end of the sensor assembly and includes a connector or fitting for fluid flow connection with a catheter for insertion into a blood vessel of the patient. A second fluid flow line extends from the upstream end of the sensor housing and similarly includes a connector or fitting for fluid flow connection with a source of fluid. One or more analytical sensors are disposed in the sensor housing in fluid communication with the first and second fluid flow lines. Conveniently, the turbulence-inducing coil of the present invention is formed in the second fluid flow line as part of the sensor module, immediately upstream from the sensor housing.

Other features and advantages of the invention should become apparent from the following description of the preferred embodiments, taken in conjunction with the accompanying drawings, which illustrate, by way of example, the principles of the invention.

BRIEF DESCRIPTION OF THE DRAWINGS

FIG. 1 is a diagrammatic illustration of a combined infusion delivery and blood chemistry measurement system embodying the method and apparatus of the present invention; and FIG. 2 is a plan view of a blood chemistry sensor module, with a turbulence-inducing coil formed in the fluid flow line immediately upstream from the blood chemistry sensor assembly.

DESCRIPTION OF THE PREFERRED EMBODIMENT

With reference now to the drawings for purposes of illustration, and particularly to FIG. 1 thereof, there is shown a system for infusing an infusion fluid into a patient 11 while intermittently monitoring a number of parameters of the patient's blood. The system includes an infusion pump 13 for pumping the infusion fluid in a forward direction from an infusion fluid source 15 to the patient, via an infusion tube 17, a blood chemistry sensor assembly 19 and a catheter 21. The infusion fluid preferably is a physiological isotonic saline solution of appropriate concentration, although the fluid also may incorporate selected nutrients or medications for delivery to the patient.

At appropriate times, a system controller 23 causes the infusion pump 13 to reverse its direction, and instead to draw blood from the patient 11 through the catheter 21 and into the sensor assembly 19. This reversal of the pump's direction may occur at predetermined time intervals, or upon receipt by the controller of a manual command issued by a caregiver.

The sensor assembly 19 contains a number of analytical sensors, each of which produces a signal indicative of a separate parameter of the patient's blood. Examples of such parameters include concentrations of carbon dioxide, oxygen, potassium, calcium, and sodium. Other parameters that can be sensed by such sensors include hematocrit, temperature, and pH. To perform the desired analysis, a sample of the patient's blood must be drawn into a position where it contacts all of the analytical sensors of the sensor assembly. In addition, sufficient additional blood should be drawn to minimize the effects of any dilution of the blood by the adjacent infusion fluid. As a result, the blood sample preferably is drawn entirely through the sensor assembly and into the fluid flow line above the sensor assembly.

After the patient's blood sample has been drawn to the appropriate position, electrical signals from the various analytical sensors are read and analyzed by an analyzer 25. Preferably, a brief stabilization period is allowed to elapse before the sensors are read. This period typically is in the range of 10 to 90 seconds. The analyzer converts the electrical signals from the sensors into corresponding indications of the concentrations of one or more components, or of other parameters, of the patient's blood. These indications can be read by a caregiver monitoring the patient.

Thereafter, after the analysis has been completed, the controller 23 again operates the pump 13 in its forward direction, to flush the blood sample out of the sensor assembly 19 and back into the patient 11. Normal pumping of the infusion fluid into the patient then resumes. This pumping can occur at a relatively low flow rate of about 1 to 10 milliliters per hour.

Referring now to FIG. 2, the blood chemistry sensor assembly 19 is a modular unit adapted to be installed in the fluid flow line 17 of a standard IV infusion set. The sensor assembly includes an elongate housing 27, which in FIG. 2 is shown with its cover removed to expose a plurality of analytical sensors 29a–29c and 31a–31d disposed in first and second chambers 33 and 35, respectively. Each sensor is positioned adjacent to a fluid pathway (not shown) that extends through the chambers.

A first fluid flow line 37 connects to the downstream end of the fluid pathway and then extends from the downstream end of the sensor housing 27. The free end of the first fluid flow line has a standard connector 39 which is adapted for flow connection to the catheter 21 shown in FIG. 1. A second fluid flow line 41 connects to the upstream end of the fluid pathway, is looped in serpentine fashion back around a cylindrical post 43 mounted generally centrally within the sensor housing 27, and then extends from the upstream end of the housing 27. This serpentine portion of fluid flow line typically holds about 0.3 ml of fluid to enable pre-heating of it prior to infusion into the patient. The free end of the second fluid flow line 41 similarly has a standard connector 45 which is adapted for mating to a connector (not shown) at the end of the fluid flow line leading from the infusion fluid source 15 shown in FIG. 1.

In accordance with the invention, a coil 47 is formed in the second fluid flow line 41, immediately upstream from the sensor assembly 19, by looping the second fluid flow line around on itself. As shown in FIG. 2, the coil has five loops with a diameter between 0.75 and 1.0 inch formed in a spiral. This coil can be formed by winding the fluid flow line around a mandrel and heating the polyvinyl chloride (PVC) material of the fluid flow line to a temperature slightly above its glass transition temperature (e.g., 110° C.). Upon cooling, the fluid flow line will retain its coiled form permanently.

As mentioned above, in operation of the blood chemistry monitoring system of FIG. 1, a blood sample is drawn from the patient 11 entirely through the sensor assembly 19 and into the fluid flow line upstream from the sensor assembly. For example, it has been found preferable to draw about 1.0 ml of blood beyond the amount minimally necessary to fill the two chambers 33 and 35 containing the analytical sensors 29a–29c and 31a–31d, respectively, in the sensor assembly. Since, as noted, the serpentine portion of the second fluid flow line 41 disposed within the housing 27 typically holds only 0.3 ml of fluid, this overdraw results in the blood sample reaching about one-half to three-quarters through the length of the coil 47 in the second fluid flow line 41.

When the controller 23 again operates the pump 13 in its forward direction to flush the blood sample and back into the patient 11, after the analysis is complete, the coil 47 will impart a rotational motion to the blood. This motion generates turbulence in the fluid flow to help purge the patient's blood both from the fluid flow line and the fluid pathway through the sensor assembly 19. The purging action in the fluid pathway is enhanced by the fact that the cross-sectional area of the fluid pathway is significantly smaller than the cross-sectional area of the second fluid flow line 41 in which the coil is formed, resulting in an increased velocity of the fluid flow through the fluid pathway.

As a result of the turbulence induced by the coil 47, it has been found that the blood sample can be cleared from the fluid flow line and the sensor assembly with just 3 to 4 ml of saline (i.e., 2 to 3 times the sample blood volume drawn), at a purge rate of 900 ml/hr. Without the coil, it would require at least 8 to 9 ml of saline to clear the blood sample at that purge rate. Thus, the amount of saline required to purge blood samples is reduced through use of the invention by a factor of two to three, thereby bringing the purge volumes within the fluid intake range of many patients for whom the necessary purge volumes without use of the invention would be deemed excessive. Moreover, the economic advantage derived by using the invention is readily apparent.

It should be appreciated from the foregoing description that the present invention provides a method and apparatus for reducing the purge volume needed in a blood chemistry monitoring system, with attendant clinical and economic benefits. Those of ordinary skill in the art will further appreciate that the present invention may have application to a variety of devices for sampling bodily fluids where conservation of fluid flushing volumes is a concern. Even in standard A-line IV infusion sets, the present invention can be added immediately upstream from a blood sampling port.

A preferred embodiment of method and apparatus for reducing purge volume in a blood chemistry monitoring system has been described in detail for purposes of understanding and illustration. Various additions and modifications will no doubt occur to those skilled in the art without departing from the principles of the invention. Therefore, the scope of the invention should be determined primarily with reference to the appended claims, along with the full scope of equivalents to which those claims are legally entitled.

What is claimed is:

1. Apparatus for monitoring a predetermined parameter of a patient's blood while infusing an infusion fluid into the patient, comprising:

a sensor assembly having an upstream end and a downstream end;

a first fluid flow line extending from the downstream end of the sensor assembly and including a connector for connecting the first fluid flow line in fluid communication with a catheter configured for insertion into a blood vessel of the patient;

a second fluid flow line extending from the upstream end of the sensor assembly and including a connector for connecting the second fluid flow line in fluid communication with a source of fluid, wherein the second fluid flow line has a coil formed therein by looping the line around on itself;

a pump conditioned to pump the infusion fluid from the source of fluid to the patient, through the second fluid flow line, the sensor assembly, and the first fluid flow line, and further conditioned to intermittently draw blood from the patient through the first fluid flow line and the sensor assembly and into, but not beyond, the coil of the second fluid flow line; and one or more sensors, disposed in the sensor assembly in fluid communication with the first and second fluid flow lines, for providing a signal indicative of a predetermined parameter of a patient's blood when drawn into the sensor assembly;

wherein the coil of the second fluid flow line is configured to generate turbulence in the fluid flow, to help purge the patient's blood from the sensor assembly after sampling.

2. Apparatus as set forth in claim 1, wherein the coil in the second fluid flow line comprises a series of loops formed in a spiral.

3. Apparatus as defined in claim 1, wherein:

the coil of the second fluid flow line is located immediately adjacent to the sensor assembly; and the pump is conditioned to draw blood from the patient as far as a point about one-half to three-quarters through the length of the coil of the second fluid flow line.

4. Apparatus for monitoring a predetermined parameter of a patient's blood while infusing an infusion fluid into the patient, comprising:

a source of fluid;

a fluid flow line in fluid communication with the source of fluid, for infusing fluid into the patient;

a sensor assembly in fluid communication with the fluid flow line;

wherein a coil is formed in the fluid flow line between the source of fluid and the sensor assembly by looping the fluid flow line around on itself; and a pump conditioned to pump the infusion fluid from the source of fluid to the patient, through the fluid flow line and the sensor assembly, and further conditioned to intermittently draw blood from the patient through the fluid flow line and the sensor assembly and into, but not beyond, the coil of the fluid flow line, whereupon the sensor assembly senses characteristics of the blood;

wherein the coil of the fluid flow line is configured to generate turbulence in the fluid flow to help purge the patient's blood from the sensor assembly after sampling.

5. Apparatus as set forth in claim 4, wherein the coil is looped around on itself more than once to form a plurality of loops in the fluid flow line.

6. Apparatus as set forth in claim 5, wherein the coil comprises a series of loops formed in a spiral.

7. Apparatus as set forth in claim 5, wherein the coil comprises at least three loops of the fluid flow line.

8. Apparatus as set forth in claim 4, wherein the coil in the fluid flow line comprises one or more loops having a diameter of less than about two inches.

9. Apparatus as defined in claim 4, wherein:

the coil of the fluid flow line is located immediately adjacent to the sensor assembly; and the pump is conditioned to draw blood from the patient as far as a point about one-half to three-quarters through the length of the coil of the fluid flow line.

10. A method for measuring one or more predetermined parameters of a patient's blood, comprising steps of:

providing a sensor assembly having one or more sensors, each configured to measure a predetermined parameter of an adjacent fluid;

connecting the sensor assembly to an infusion line, such that a pump can direct an infusion fluid through the infusion line to the sensor assembly and, in turn, into the patient's vascular system, wherein a predetermined portion of the infusion line is configured in the shape of a coil, to induce turbulence in any fluid flowing through it;

intermittently conditioning the pump to draw blood from the patient through the sensor assembly and into, but not beyond, the predetermined portion of the infusion line, whereupon the one or more sensors of the sensor assembly can measure the one or more predetermined parameters of the patient's blood; and thereafter conditioning the pump to purge the drawn blood from the infusion line and sensor assembly, back into the patient's vascular system, wherein the coil of the infusion line ensures that the infusion fluid passing therethrough is sufficiently turbulent to help purge the blood from the infusion line and the sensor assembly.

11. A method as defined in claim 10, wherein:

the coil of the infusion line is located immediately adjacent to the sensor assembly; and the step of intermittently conditioning the pump to draw blood from the patient includes a step of drawing blood as far as a point about one-half to three-quarters through the length of the coil of the infusion line.

* * * * *